US009271948B2

(12) United States Patent
Hayashi et al.

(10) Patent No.: US 9,271,948 B2
(45) Date of Patent: Mar. 1, 2016

(54) AGENT FOR IMPROVING VESICOURETHRAL DYSSYNERGIA

(71) Applicant: TAIHO PHARMACEUTICAL CO., LTD., Tokyo (JP)

(72) Inventors: Yukio Hayashi, Tsukuba (JP); Atsushi Hakozaki, Tsukuba (JP)

(73) Assignee: Taiho Pharmaceutical Co., Ltd., Tokyo (JP)

(*) Notice: Subject to any disclaimer, the term of this patent is extended or adjusted under 35 U.S.C. 154(b) by 0 days.

(21) Appl. No.: 14/496,281

(22) Filed: Sep. 25, 2014

(65) Prior Publication Data

US 2015/0094380 A1    Apr. 2, 2015

(30) Foreign Application Priority Data

Sep. 27, 2013  (JP) ................................ 2013-201442
Dec. 26, 2013  (JP) ................................ 2013-269161

(51) Int. Cl.
    *A61K 31/122*    (2006.01)
(52) U.S. Cl.
    CPC .................................... *A61K 31/122* (2013.01)
(58) Field of Classification Search
    CPC .................................................. A61K 31/122
    See application file for complete search history.

(56) References Cited

U.S. PATENT DOCUMENTS 6,906,107 B2    6/2005    Miyagawa et al.

FOREIGN PATENT DOCUMENTS

| JP | 3836684 A   | 8/2006 |
|----|-------------|--------|
| WO | 99/08987 A1 | 2/1999 |
| WO | 9908987 A1  | 2/1999 |
| WO | 02/066024 A1| 8/2002 |

OTHER PUBLICATIONS

Saito et al., "Effect of cyclohexenonic long-chain fatty alcohol on rat overactive bladder induced by bladder neck obstruction", European Journal of Pharmacology, vol. 501, No. 1-3, Oct. 2004, pp. 143-149.
Supplementary European Search Report dated Jan. 29, 2015 for EP Patent Application No. 14186615.2, 5 pages.
Jorgensen et al., "Idiopathic Detrusor Sphincter Dyssynergia in Neurologically Normal Patients with Voiding Abnormalities" Eur. Urol., 1982, vol. 8, pp. 107-110.
Kitami, "Vesicourethral Dysfunction of Diabetic Patients", The Japanese Journal of Urology, 1991, vol. 82, No. 7, pp. 1074-1083.

Minardi et al., "Sacral neuromodulation in patients with multiple sclerosis", World J. Urol., 2012, vol. 30, pp. 123-128.
Murayama, Hainyo-Shogai Practice (Dysuria Practice), 2001, vol. 9, No. 2, pp. 111-115 (Abstract).
Nakai et al, "Correlation Between Lower Urinary Tract Symptoms and Urethral Function in Benign Prostatic Hyperplasia", Neurourology and Urodynamics, 2004, vol. 23, pp. 618-622.
Saito et al., "Ability of Cyclohexenonic Long-Chain Fatty Alcohol to Reverse Diabetes-Induced Cystopathy in the Rat", European Urology, 2007, vol. 51, No. 2, pp. 479-488 (a corresponding Office Action dated Mar. 4, 2014 in JP 2013-269161).
Shiina et al, "Vesicourethral Function after Surgery for Uterine Cancer: Predictive Value of Postoperative Maximum Urethral Closure Pressure on Residual Urine", Urol. Int., 1993, vol. 51, pp. 125-128.
Tosaka et al., "Video Urodynamics Using Transrectal Ultrasonography for Lower Urinary Tract Symptoms in Women", Neurourology and Urodynamics, 2003, vol. 22, pp. 33-39.
Weld et al., "Association of Level of Injury and Bladder Behavior in Patients with Post-Traumatic Spinal Cord Injury", Urology, 2000, vol. 55, No. 4, pp. 490-494.
Abrams et al., "The Standardisation of Terminology of Lower Urinary Tract Function: Report from the Standardisation Sub-committee of the International Continence Society" Neurourology and Urodynamics, 2002, vol. 21, pp. 167-178.
Goi et al., "Effects of Silodosin, a Selective α1A-Adrenoceptor Antagonist, on Bladder Blood Flow and Bladder Function in a Rat Model of Atherosclerosis Inducted Chronic Bladder Ischemia without Bladder Outlet Obstruction", The Journal of Urology, 2013, vol. 190, pp. 1116-1122.
Gomes et al, "Voiding Dysfunction and Urodynamic Abnormalities in Elderly Patients", Rev. Hosp. Clin. Fac. Med. Sao Paulo, 2004, vol. 59, No. 4, pp. 206-215.
Hashimoto et al., "Effects of the Selective Acetylcholinesterase InhibitorTAK-802 on the Voiding Behavior and Bladder Mass Increase in Rats with Partial Bladder Outlet Obstruction", The Journal of Urology, 2005, vol. 174, pp. 1137-1141.

(Continued)

*Primary Examiner* — Wu-Cheng Winston Shen
*Assistant Examiner* — Christopher R Stone
(74) *Attorney, Agent, or Firm* — Rothwell, Figg, Ernst & Manbeck, P.C.

(57) ABSTRACT

This invention is directed to an ameliorating agent for a disease based on vesicourethral dyssynergia, comprising, as an active ingredient, 3-(15-hydroxypentadecyl)-2,4,4-trimethyl-2-cyclohexene-1-one, a salt thereof, or a solvate thereof. The disease based on vesicourethral dyssynergia is any of dysuria accompanying a lifestyle-related disease (such as diabetic dysuria), idiopathic dysuria, dysuria after pelvic surgery, dysuria accompanying spinal cord injury, dysuria accompanying spinal canal stenosis, dysuria accompanying benign prostatic hypertrophy, dysuria accompanying high-pressure voiding/high-pressure urine storage, neurogenic or nonneurogenic lower urinary tract symptoms (LUTS), detrusor sphincter dyssynergia, and detrusor bladder neck dyssynergia.

2 Claims, 3 Drawing Sheets

(56) References Cited

OTHER PUBLICATIONS

Haylen et al., "An International Urogynecological Association (IUGA)/International Continence Society (ICS) Joint Report on the Terminology for Female Pelvic Floor Dysfunction", Neurourology and Urodynamics, 2010, vol. 29, pp. 4-20.

Kaplan et al., "Tolterodine and Tamsulosin for Treatment of Men with Lower Urinary Tract Symptoms and Overactive Bladder: A Randomized Controlled Trial", JAMA, 2006, vol. 296, No. 19, pp. 2319-2328.

Kwak et al., "Inhibitory effects of propiverine, atropine and oxybutynin on bladder instability in rats with infravesical outlet obstruction", British Journal of Urology, 1998, vol. 82, pp. 272-277.

Maruyama et al., "Effects of ritobegron (KUC-7483), a novel $\beta 3$-adrenoceptor agonist, on both rat bladder function following partial bladder outlet obstruction and on rat salivary secretion" a comparison with the effects of tolterodine, Journal of Smooth Muscle Research, 2012, vol. 48, No. 5&6 pp. 115-124.

Osman et al., "Detrusor Underactivity and the Underactive Bladder: A New Clinical Entity? A Review of Current Terminology, Definitions, Epidemiology, Aetiology, and Diagnosis", European Urology, 2014, vol. 65, pp. 389-398.

Resnick et al., "Detrusor Hyperactivity with Impaired Contractile Function", JAMA, 1987, vol. 257, No. 22, pp. 3076-3081.

Schäfer, Principles and Clinical Application of Advanced Urodynamic Analysis of Voiding Functioning, Urologic Clinics of North America, 1990, vol. 17, No. 3, pp. 553-566.

AGENT FOR IMPROVING VESICOURETHRAL DYSSYNERGIA

TECHNICAL FIELD

The present invention relates to a vesicourethral dyssynergia ameliorating agent comprising, as an active ingredient, 3-(15-hydroxypentadecyl)-2,4,4-trimethyl-2-cyclohexene-1-one, a salt thereof, or a solvate thereof; and a pharmaceutical composition for treating a disease based on vesicourethral dyssynergia.

The present invention also relates to a method for ameliorating vesicourethral dyssynergia, a method for treating a disease based on vesicourethral dyssynergia, and a method for ameliorating time lag between bladder contraction and urethra relaxation.

The present invention further relates to 3-(15-hydroxypentadecyl)-2,4,4-trimethyl-2-cyclohexene-1-one, a salt thereof, or a solvate thereof for use in the treatment of a disease based on vesicourethral dyssynergia.

BACKGROUND ART 3-(15-hydroxypentadecyl)-2,4,4-trimethyl-2-cyclohexene-1-one (hereinafter referred to as "Compound 1 of the present invention") is a compound having a structure represented by Formula (1) below.

[Chem. 1]

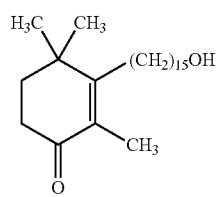

(1)

Patent Document 1 discloses that a cyclohexenone long-chain alcohol comprising the compound represented by Formula (1) has an effect of promoting neurite growth, and thus is useful as a preventive and/or therapeutic agent for brain disorders such as dementia. Patent Document 2 discloses that a cyclohexenone long-chain alcohol comprising the compound represented by Formula (1) is useful as a therapeutic agent for treating dysuria.

However, the effect as a therapeutic agent for treating dysuria shown in Patent Document 2 was confirmed only against dysuria with bladder dysfunction (the effect was confirmed by the improvement in maximum voided volume, and the improvement in bladder capacity and micturition efficiency), and the maximum voided volume was lower than that of the streptozotocin (STZ) administration group. More specifically, the effect of ameliorating vesicourethral dyssynergia of Compound 1 of the present invention has been completely unknown.

Vesicourethral dyssynergia is a type of dysuria caused by the timing difference between the contraction of bladder detrusor and the relaxation of urethral sphincter. Normally, the contraction of detrusor and the relaxation of urethral sphincter cooperate, and the contraction of detrusor occurs in conjunction with the relaxation of urethral sphincter, thus enabling smooth micturition. However, when the cooperation of the contraction of detrusor and the urethral sphincter is impaired and an apparent timing difference (time lag) is thus generated between the contraction of the detrusor and the relaxation of the urethral sphincter, high-pressure voiding, residual urine after micturition, or urinary incontinence occurs even when the time lag is only several seconds. Further, if such a condition is left unattended without appropriate care, it results in urinary-tract infection, upper urinary tract disorder, or renal dysfunction. Therefore, amelioration of this time lag is an important objective in the treatment of diseases based on vesicourethral dyssynergia.

In a broad sense, the definition of vesicourethral dyssynergia includes detrusor sphincter dyssynergia, and detrusor bladder neck dyssynergia.

Examples of known diseases based on vesicourethral dyssynergia include dysuria accompanying a lifestyle-related disease (such as diabetic dysuria) (Non-patent Document 1), idiopathic dysuria (Non-patent Document 2), dysuria after pelvic surgery (Non-patent Document 3), dysuria accompanying spinal cord injury, spinal canal stenosis, benign prostatic hypertrophy, and the like (Non-patent Document 4, Non-patent Document 5, and Non-patent Document 6), dysuria accompanying high-pressure voiding/high-pressure urine storage, and neurogenic or nonneurogenic lower urinary tract symptoms (LUTS) (Non-patent Document 7, and Non-patent Document 8).

CITATION LIST

Patent Documents

Patent Document 1: International Publication WO1999/008987
Patent Document 2: International Publication WO2002/066024

Non-Patent Documents

Non-patent Document 1: Nihon Hinyokika Gakkai Zasshi., 82, p. 1074-1083 (1991)
Non-patent Document 2: Eur Urol., 8, p. 107-110 (1982)
Non-patent Document 3: Urol Int., 51, p. 125-128 (1993)
Non-patent Document 4: Urology, 55, p. 490-494 (2000)
Non-patent Document 5: *Hainyo-Shogai Practice* [Voiding dysorders digest], 9, p. 111-115 (2001)
Non-patent Document 6: Neurourol. Urodyn., 23, p. 618-622 (2004)
Non-patent Document 7: World Urol., 30, p. 123-128 (2012)
Non-patent Document 8: Neurourol. Urodyn., 22, p. 33-39 (2003)

SUMMARY OF INVENTION

Technical Problem

The therapeutic agent with either the effect of enhancing the contraction ability of the bladder detrusor or the effect of relaxing the urethral sphincter had a clinically insufficient effect on patients having vesicourethral dyssynergia.

An object of the present invention is to provide a therapeutic agent for treating a disease based on vesicourethral dyssynergia by improving the cooperation of the bladder detrusor and the urethral sphincter, a method for ameliorating vesicourethral dyssynergia, a pharmaceutical composition, a method for treating a disease based on vesicourethral dyssynergia, a method for ameliorating time lag between bladder contraction and urethra relaxation, and a compound for use in the treatment of a disease based on vesicourethral dyssynergia.

Solution to Problem

The inventors of the present invention carried out extensive research to attain the above object, and found that 3-(15-hydroxypentadecyl)-2,4,4-trimethyl-2-cyclohexene-1-one represented by Formula (1) below ameliorates vesicourethral dyssynergia, and thus is useful as a therapeutic agent for treating a disease based on vesicourethral dyssynergia.

[Chem. 1]

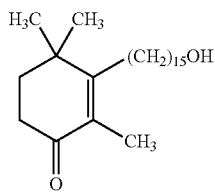

(1)

More specifically, the present invention provides a vesicourethral dyssynergia ameliorating agent comprising, as an active ingredient, 3-(15-hydroxypentadecyl)-2,4,4-trimethyl-2-cyclohexene-1-one, a salt thereof, or a solvate thereof. The disease based on vesicourethral dyssynergia is any of dysuria accompanying a lifestyle-related disease (such as diabetic dysuria), idiopathic dysuria, dysuria after pelvic surgery, dysuria accompanying spinal cord injury, dysuria accompanying spinal canal stenosis, dysuria accompanying benign prostatic hypertrophy, dysuria accompanying high-pressure voiding/high-pressure urine storage, neurogenic or nonneurogenic lower urinary tract symptoms (LUTS), detrusor sphincter dyssynergia, and detrusor bladder neck dyssynergia.

Further, the present invention provides a vesicourethral dyssynergia ameliorating agent comprising, as an active ingredient, 3-(15-hydroxypentadecyl)-2,4,4-trimethyl-2-cyclohexene-1-one, a salt thereof, or a solvate thereof.

Further, the present invention provides a pharmaceutical composition for treating a disease based on vesicourethral dyssynergia comprising 3-(15-hydroxypentadecyl)-2,4,4-trimethyl-2-cyclohexene-1-one, a salt thereof, or a solvate thereof, and a pharmaceutically acceptable carrier. The disease based on vesicourethral dyssynergia is any of dysuria accompanying a lifestyle-related disease (such as diabetic dysuria), idiopathic dysuria, dysuria after pelvic surgery, dysuria accompanying spinal cord injury, dysuria accompanying spinal canal stenosis, dysuria accompanying benign prostatic hypertrophy, dysuria accompanying high-pressure voiding/high-pressure urine storage, neurogenic or nonneurogenic lower urinary tract symptoms (LUTS), detrusor sphincter dyssynergia, and detrusor bladder neck dyssynergia.

Further, the present invention provides a vesicourethral dyssynergia ameliorating method comprising administering a therapeutically effective amount of 3-(15-hydroxypentadecyl)-2,4,4-trimethyl-2-cyclohexene-1-one, a salt thereof, or a solvate thereof to a patient having a disease based on vesicourethral dyssynergia.

Further, the present invention provides a method for treating a disease based on vesicourethral dyssynergia selected from the group consisting of dysuria accompanying a lifestyle-related disease (such as diabetic dysuria), idiopathic dysuria, dysuria after pelvic surgery, dysuria accompanying spinal cord injury, dysuria accompanying spinal canal stenosis, dysuria accompanying benign prostatic hypertrophy, dysuria accompanying high-pressure voiding/high-pressure urine collection, neurogenic or nonneurogenic lower urinary tract symptoms (LUTS), detrusor sphincter dyssynergia, and detrusor bladder neck dyssynergia, the method comprising the step of administering a therapeutically effective amount of 3-(15-hydroxypentadecyl)-2,4,4-trimethyl-2-cyclohexene-1-one, a salt thereof, or a solvate thereof to a patient.

Further, the present invention provides a method for treating vesicourethral dyssynergia, comprising the step of administering a therapeutically effective amount of 3-(15-hydroxypentadecyl)-2,4,4-trimethyl-2-cyclohexene-1-one, a salt thereof, or a solvate thereof, to a patient.

Further, the present invention provides a method for ameliorating time lag between the bladder contraction and the urethra relaxation, the method comprising the step of administering 3-(15-hydroxypentadecyl)-2,4,4-trimethyl-2-cyclohexene-1-one, a salt thereof, or a solvate thereof to a test subject having a time lag between bladder contraction and urethra relaxation in an effective amount for ameliorating the time lag.

Further, the present invention provides use of 3-(15-hydroxypentadecyl)-2,4,4-trimethyl-2-cyclohexene-1-one, a salt thereof, or a solvate thereof for the manufacture of a therapeutic agent for a disease based on vesicourethral dyssynergia selected from the group consisting of dysuria accompanying a lifestyle-related disease (such as diabetic dysuria), idiopathic dysuria, dysuria after pelvic surgery, dysuria accompanying spinal cord injury, dysuria accompanying spinal canal stenosis, dysuria accompanying benign prostatic hypertrophy, dysuria accompanying high-pressure voiding/high-pressure urine storage, neurogenic or nonneurogenic lower urinary tract symptoms (LUTS), detrusor sphincter dyssynergia, and detrusor bladder neck dyssynergia.

Further, the present invention provides 3-(15-hydroxypentadecyl)-2,4,4-trimethyl-2-cyclohexene-1-one, a salt thereof, or a solvate thereof for use in the treatment of a disease based on vesicourethral dyssynergia selected from the group consisting of dysuria accompanying a lifestyle-related disease (such as diabetic dysuria), idiopathic dysuria, dysuria after pelvic surgery, dysuria accompanying spinal cord injury, dysuria accompanying spinal canal stenosis, dysuria accompanying benign prostatic hypertrophy, dysuria accompanying high-pressure voiding/high-pressure urine storage, neurogenic or nonneurogenic lower urinary tract symptoms (LUTS), detrusor sphincter dyssynergia, and detrusor bladder neck dyssynergia.

Advantageous Effects of Invention

The present invention enables effective treatments of vesicourethral dyssynergia, and diseases based on vesicourethral dyssynergia.

DESCRIPTION OF EMBODIMENTS

Figure 1:
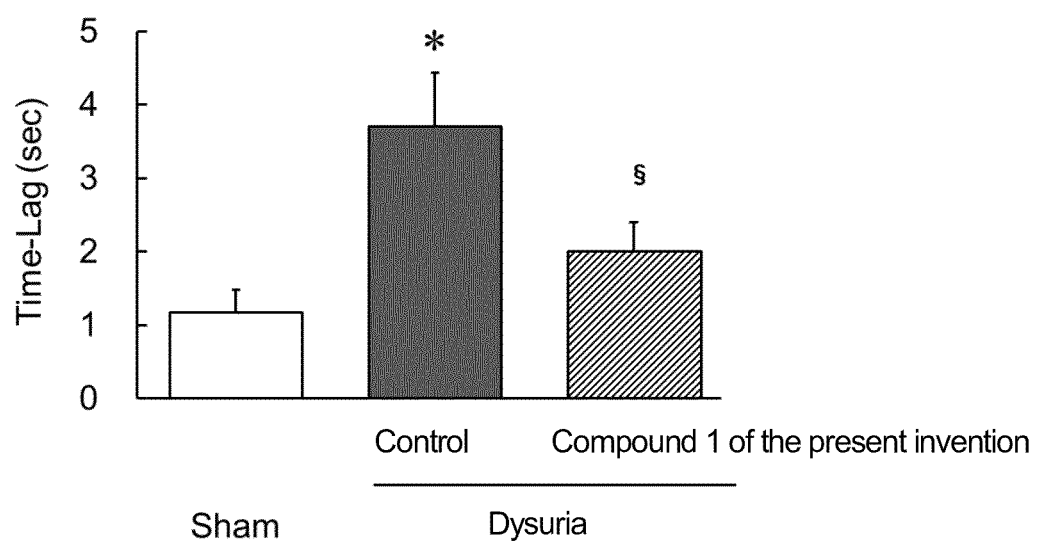
FIG. 1 shows the effect of Compound 1 of the present invention on vesicourethral dyssynergia in a dysuria model rat.
Sham: n=8, Control (6% Gelucire): n=9, Compound 1 of the present invention (30 mg/kg×2/day p.o.): n=10
*: $p<0.05$ vs. Sham group (Wilcoxon test)
§: $p<0.05$ vs. Control group (unpaired Student's t-test)

Micturition is performed by the cooperation of the contraction of bladder detrusor and the relaxation of urethral sphincter. Even when the bladder detrusor contracts, normal micturition cannot be performed if the urethral sphincter also contracts at the same time. Similarly, even when the urethral sphincter relaxes, normal micturition cannot be performed unless the bladder detrusor contracts. Dysuria includes a failure of contraction of bladder detrusor and a failure of relaxation of urethral sphincter; however, the target disease treatable by the present invention is vesicourethral dyssynergia, i.e., dysuria caused by an apparent time lag, i.e., the timing difference between the contraction of bladder detrusor and the relaxation of urethral sphincter.

Measurement of electromyography (EMG) of external urethral sphincter, and pressure-flow study are useful for the detection, evaluation, or diagnosis of vesicourethral dyssynergia. Further, the evaluation of the urethral state upon micturition using voiding cystourethrography (VCUG) also enables presumption of the presence of vesicourethral dyssynergia. The detection of abnormal enlargement of the posterior urethra and the backflow into the prostate gland strongly suggest the presence of vesicourethral dyssynergia.

Compound 1 of the present invention is a known compound, and is produced by, for example, the method disclosed in International Publication WO1999/008987.

The term "treatment" in the present invention means prevention of the extension of the time lag between the bladder contraction and the urethra relaxation (prophylaxis), reduction in the time lag between the bladder contraction and the urethra relaxation (treatment), and a maintenance treatment for alleviating the symptoms and preventing the recurrence by the reduction of the time lag between the bladder contraction and the urethra relaxation (continuation of the reduced time lag).

Examples of "diseases based on vesicourethral dyssynergia treatable by the compound or the pharmaceutical composition of the present invention" include various diseases caused by vesicourethral dyssynergia, such as urine storage disorder or dysuria; more preferably overactive bladder, detrusor hyperreflexia, detrusor hyperreflexia with impaired contractile function (DHIC), underactive bladder, underactive detrusor, and urinary incontinence; and further preferably dysuria accompanying a lifestyle-related disease (such as diabetic dysuria), idiopathic dysuria, dysuria after pelvic surgery, dysuria accompanying spinal cord injury, dysuria accompanying spinal canal stenosis, dysuria accompanying benign prostatic hypertrophy, dysuria accompanying high-pressure voiding/high-pressure urine storage, neurogenic or nonneurogenic lower urinary tract symptoms (LUTS), detrusor sphincter dyssynergia, and detrusor bladder neck dyssynergia. If these diseases are not accompanied by vesicourethral dyssynergia, they fall out of the range of diseases treatable by the present invention.

In the present specification, the phrase "ameliorate vesicourethral dyssynergia" means reducing the time lag between the bladder contraction and the urethra relaxation by improving the cooperation of the bladder detrusor and the urethral sphincter. The reduction in the time lag between the bladder contraction and the urethra relaxation results in amelioration of diseases based on vesicourethral dyssynergia, such as dysuria accompanying a lifestyle-related disease (such as diabetic dysuria), idiopathic dysuria, dysuria after pelvic surgery, dysuria accompanying spinal cord injury, dysuria accompanying spinal canal stenosis, dysuria accompanying benign prostatic hypertrophy, dysuria accompanying high-pressure voiding/high-pressure urine storage, neurogenic or nonneurogenic lower urinary tract symptoms (LUTS), detrusor sphincter dyssynergia, detrusor bladder neck dyssynergia, and the like.

Examples of the solvent of the solvate of 3-(15-hydroxypentadecyl)-2,4,4-trimethyl-2-cyclohexene-1-one include water, methanol, ethanol, isopropanol, acetonitrile, tetrahydrofuran, ethyl acetate, toluene, hexane, acetone, methyl ethyl ketone, and methyl isobutyl ketone.

3-(15-hydroxypentadecyl)-2,4,4-trimethyl-2-cyclohexene-1-one, a salt thereof, or a solvate thereof of the present invention can be prepared into various dosage forms by using known preparation methods using a pharmaceutically acceptable carrier. The dosage form is not particularly limited, and examples thereof include oral agents such as tablets, coated tablets, pills, powdered drugs, granules, capsules, liquids, suspensions, or emulsions; and parenteral agents such as injections or suppositories.

In preparing tablets, examples of carrier include excipients such as lactose, sucrose, sodium chloride, glucose, urea, starch, calcium carbonate, kaolin, crystalline cellulose, or silicic acid; binders such as water, ethanol, propanol, cornstarch, simple syrup, glucose solution, starch solution, gelatin solution, carboxymethylcellulose, shellac, methylcellulose, hydroxypropylcellulose, hydroxypropylmethylcellulose, potassium phosphate, or polyvinyl pyrrolidone; disintegrants such as dry starch, sodium alginate, powdered agar, powdered laminaran, sodium hydrogencarbonate, calcium carbonate, polyoxyethylene sorbitan fatty acid ester, sodium lauryl sulfate, stearic acid monoglyceride, or lactose; disintegration inhibitors such as sucrose, stearic acid, cacao butter, or hydrogenated oils; absorbefacients such as quaternary ammonium salts or sodium lauryl sulfate; moisturizers such as glycerin or starch; adsorbents such as starch, lactose, kaolin, bentonite, or colloidal silicic acid; and lubricants such as purified talc, stearate, boric acid powder, or polyethylene glycol. Further, the tablets may be generally coated tablets such as sugar-coated tables, gelatin-coated tablets, enteric-coated tablets, film-coated tablets, double-coated tablets, or multi-coated tablets.

In preparing pills, examples of the carrier include excipients such as glucose, lactose, starch, cacao butter, hardened vegetable oil, kaolin, or talc; binders such as gum arabic powder, tragacanth powder, gelatin, or ethanol; and disintegrators such as laminaran or agar. Capsules are usually prepared in a standard method by blending the drug with one or more carriers as exemplified above, and encapsulating the mixture into hard gelatin capsules, soft capsules, etc.

In preparing oral liquid formulations, an internal liquid medicine, a syrup, an elixir, or the like, may be prepared by a standard method using sweetening/flavoring agent, buffer, stabilizer, etc. In this case, examples of sweetening/flavoring agents include sucrose, wild orange peel, citric acid, and tartaric acid; examples of buffers include sodium citrate; and examples of stabilizers include tragacanth, gum arabic, and gelatin.

In preparing suppositories, examples of usable carriers include polyethylene glycol, cacao butter, higher alcohols, esters of higher alcohols, gelatin, and semisynthetic glycerides.

In preparing injections, the liquids, emulsions, and suspensions are preferably sterilized and rendered isotonic to the blood. Examples of diluents for preparing such dosage forms include water, aqueous lactic acid solution, ethanol, propylene glycol, macrogols, ethoxylated isostearyl alcohol, polyoxyethylenated isostearyl alcohol, and polyoxyethylene sorbitan fatty acid ester.

In this case, sodium chloride, glucose, or glycerin in an amount sufficient to prepare an isotonic solution may be added to the pharmaceutical formulation. Further, general solubilizers, buffers, anesthetics, and the like, may also be added to the pharmaceutical formulation. Additionally, coloring agents, preservatives, aromatics, flavors, sweetening agents, or other medicinal products may be incorporated, if necessary, into the pharmaceutical formulations.

The method for administering the vesicourethral dyssynergia ameliorating agent of the present invention is not particularly limited, and is suitably selected according to the dosage form thereof, the age, gender, and other conditions of the patient, the severity of the symptoms of the patient, and the like. For example, tablets, pills, powdered drugs, granules, capsules, liquids, suspensions, and emulsions are orally administered. The injections are intravenously administered singly, or as a mixture with a general infusion liquid such as liquid glucose or an amino acid liquid. Further, as necessary, the injections are singly administered intra-arterially, intramuscularly, intradermally, subcutaneously, or intraperitoneally. The suppositories are intrarectally administered.

The amount of the compound of the present invention or a salt thereof to be incorporated into each of the above dosage unit form depends on the symptoms of the target patient, or depends on the drug form; however, the amount per dosage unit form is generally preferably about 0.005 to 1,000 mg, more preferably 1 to 800 mg, further preferably 5 to 500 mg for oral agents; about 0.001 to 500 mg, more preferably 0.02 to 400 mg, further preferably 1 to 250 mg for injections; and about 0.01 to 1,000 mg, more preferably 1 to 800 mg, further preferably 5 to 500 mg for suppositories. Additionally, the daily dose for an adult of the drug to be administered with the above dosage form is generally about 0.005 to 5,000 mg, preferably 0.01 to 2,000 mg, more preferably 10 to 1600 mg, further preferably 20 to 800 mg, although such doses depend on the symptom, body weight, age, gender, etc., of the patient. For each day, the daily dose is preferably taken at one time, or divided into two to four administrations.

The present invention is more specifically described below in reference to the Test Examples; however, the present invention is not limited to these examples.

EXAMPLES

Test Example 1

Effect of Ameliorating Vesicourethral Dyssynergia in Dysuria Model Rat

The effect of 3-(15-hydroxypentadecyl)-2,4,4-trimethyl-2-cyclohexene-1-one (hereinafter referred to as "Compound 1 of the present invention") on vesicourethral dyssynergia was evaluated.

The dysuria models in this example were prepared by treating 10-week-old female Wistar rats with streptozotocin (hereinafter referred to as STZ; in an amount of 65 mg/kg, i.p.). The Sham group was prepared by treating the rats with a citric acid buffer solution instead of STZ. The test drugs (vehicle: 6% Gelucire, Compound 1 of the present invention 30 mg/kg) were orally administered to each group after four weeks from the preparation of the models (at a time dysuria is assumed to be developed) twice a day for four weeks. On the day following the final administration, the intravesical and urethral pressure was measured under urethane anesthesia, thereby evaluating the cooperation of the bladder and the urethra.

FIG. 1 shows the results. In contrast to the Sham group, significant extension of the time lag between the bladder contraction and the urethra relaxation (the time interval from the beginning of the bladder contraction to the occurrence of the urethra relaxation), which is an index of vesicourethral dyssynergia, was observed in the control group. Further, in contrast to the control group receiving vehicle (6% Gelucire) having a time lag of 3.7±0.7 seconds, the time lag in the group receiving Compound 1 of the present invention was reduced to 2.0±0.4 seconds, showing a significant effect of ameliorating vesicourethral dyssynergia.

Test Example 2

Effect on Maximum Voiding Quantity in Dysuria Model Rat

The dysuria models in this example were prepared in the same manner as in Test Example 1 by treating 10-week-old female Wistar rats with STZ (65 mg/kg, i.p.). The test drugs (vehicle: 6% Gelucire, Compound 1 of the present invention 30 mg/kg) were orally administered to each group after four weeks from the preparation of the models (at a time dysuria is assumed to be developed) twice a day for four weeks. On the day following the final administration, the maximum voiding quantity was measured under urethane anesthesia.

Table 1 shows the results. In comparison with the control group receiving vehicle (6% Gelucire), the maximum quantity excreted by single micturition in the group receiving Compound 1 of the present invention was significantly increased, showing an effect on vesicourethral dyssynergia.

TABLE 1

|  | Sham | Control | Compound 1 of the present invention |
|---|---|---|---|
| Maximum voided volme (mL) | 1.45 ± 0.14 | 2.25 ± 0.68 | 4.44 ± 0.85* |

*p < 0.05 vs. control group (Williams' multiple comparison)

Comparative Example 1

Vesicourethral Dyssynergia of Dysuria Model Rat

The vesicourethral dyssynergia of the dysuria model used in the Test Examples of Patent Document 2 was evaluated. The dysuria models were prepared by treating 10-week-old female Wistar rats with STZ (65 mg/kg, i.p.). Two days after the preparation of the models, the intravesical and urethral pressure was measured under urethane anesthesia, thereby evaluating the cooperation of the bladder and the urethra.

Figure 2:
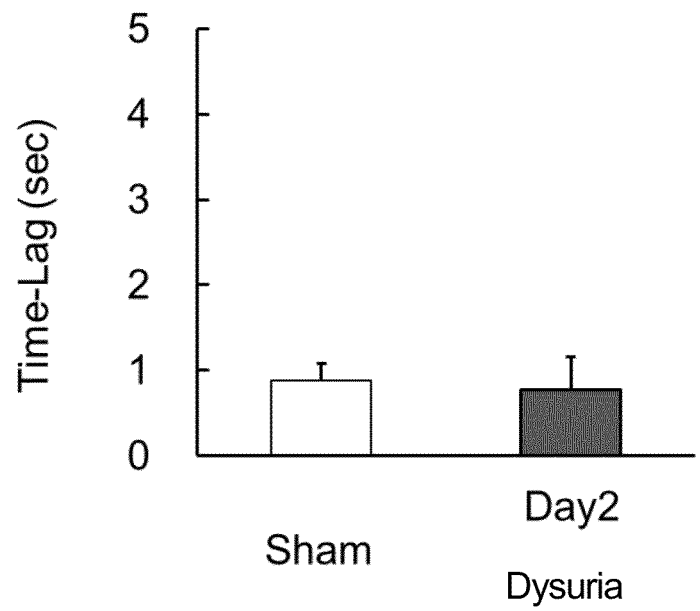
FIG. 2 shows that the time lag between the bladder contraction and the urethra relaxation, which is an index of vesicourethral dyssynergia, in comparison with the Sham group was not observed in the dysuria model used in the Test Examples of Patent Document 2.

FIG. 2 shows the results. The time lag between the bladder contraction and the urethra relaxation, which is an index of vesicourethral dyssynergia, in comparison with the Sham group was not observed two days after the preparation of the models.

Comparative Example 2

Effects of Cholinergic Agent and α1 Blocker on Vesicourethral Dyssynergia of Dysuria Model Rat The effects of a cholinergic agent (detrusor contracting agent: bethanechol) and an a1 blocker (urethra relaxation agent: tamsulosin) on vesicourethral dyssynergia were evaluated.

The dysuria models in the present example were prepared by treating 10-week-old female Wistar rats with STZ (65 mg/kg, i.p.). The Sham group was prepared by treating the rats with a citric acid buffer solution instead of STZ. Four weeks after the preparation of the models, the intravesical and urethral pressure was measured under urethane anesthesia, thereby evaluating the effects of the test drugs (vehicle: physiological saline solution, bethanechol 1 mg/kg i.v., and tamsulosin 0.3 mg/kg i.v.) with regard to the cooperation of the bladder and the urethra.

Figure 3:
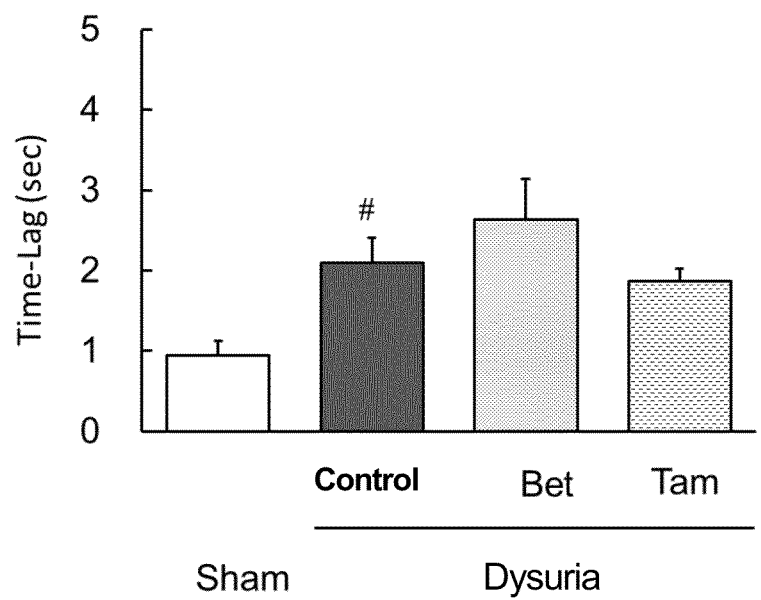
FIG. 3 shows the effects of a cholinergic agent (detrusor contracting agent: bethanechol (Bet)) and an α1 blocker (urethra relaxing agent: tamsulosin (Tam)) on vesicourethral dyssynergia in a dysuria model rat.
Sham: n=6, Control (physiological saline solution): n=11,
Bet (bethanechol, 1 mg/kg, i.v.): n=10,
Tam (tamsulosin 0.3 mg/kg, i.v.): n=10,
\#: $p<0.05$ vs Sham group (unpaired Student's t-test)

FIG. 3 shows the results. In comparison with the Sham group, significant extension of the time lag between the bladder contraction and the urethra relaxation, which is an index of vesicourethral dyssynergia (the time interval from the beginning of the bladder contraction to the occurrence of the urethra relaxation), was observed in the control group (four weeks after the development of the disease in the models). Bethanechol (Bet) and tamsulosin (Tam) showed no effects regarding the extension of the time lag between the bladder contraction and the urethra relaxation, which was observed in the control group receiving vehicle (physiological saline solution).

The above results showed that the effect of ameliorating vesicourethral dyssynergia was not observed by the administration of a cholinergic agent or an a1 blocker, which is generally used as a dysuria-treating drug. In contrast, Compound 1 of the present invention exhibited a significant effect of ameliorating vesicourethral dyssynergia compared with the control group, thereby showing that Compound 1 can serve as an effective therapeutic agent for a disease based on vesicourethral dyssynergia.

Test Example 3

Effect on Voiding Dysfunction Based on Vesicourethral Dyssynergia in Dysuria Model Rat The effect of Compound 1 of the present invention on dysuria was evaluated using a model rat having spinal cord injury, which is a typical disease causing dysuria due to vesicourethral dyssynergia.

The dysuria models in this example were prepared by placing a 40 g weight on the spinal cord in the eighth to ninth thoracic vertebrae (Th8-9) of 7-week-old female Wistar rats for 30 minutes.

The test drugs (vehicle: 6% Gelucire, Compound 1 of the present invention 250 mg/kg) were orally administered to each group from the day following the preparation of the models once a day for four weeks. On the day following the final administration, cystometry was performed in a wakeful state, thereby evaluating the voiding function (micturition efficiency).

Figure 4:
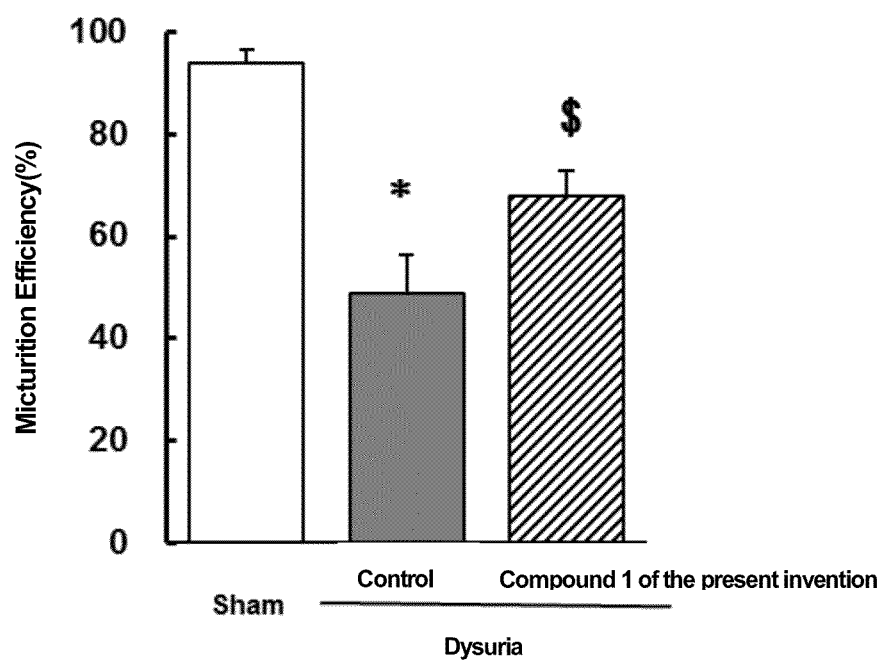
FIG. 4 shows the effect of Compound 1 of the present invention to ameliorate voiding dysfunction based on vesicourethral dyssynergia in a dysuria model rat.
Sham: n=9, Control (vehicle): n=9, Compound 1 of the present invention (250 mg/kg/day p.o.): n=11
*: $p<0.05$ vs. Sham group (Wilcoxon test)
\$: $p<0.05$ vs. Control group (unpaired Student's t-test)

As shown in FIG. 4, the micturition efficiency of the control group was significantly decreased in comparison with the Sham group, and dysuria was observed. In the group receiving Compound 1 of the present invention, a significant increase in micturition efficiency was observed in comparison with the control group.

The invention claimed is:
1. A method for treating detrusor sphincter dyssynergia in a patient in need thereof, comprising the step of administering a therapeutically effective amount of 3-(15-hydroxypentadecyl)-2,4,4-trimethyl-2-cyclohexene-1-one, a salt thereof, or a solvate thereof to said patient.
2. A method for ameliorating time lag between bladder contraction and urethra relaxation in a subject suffering from lag between bladder contraction and urethra relaxation, comprising the step of administering a therapeutically effective amount of 3-(15-hydroxypentadecyl)-2,4,4-trimethyl-2-cyclohexene-1-one, a salt thereof, or a solvate thereof in an effective amount for ameliorating the time lag to said subject.

* * * * *